United States Patent [19]

Bollin, Jr. et al.

[11] Patent Number: 4,678,812
[45] Date of Patent: Jul. 7, 1987

[54] TREHALOSE AS STABILIZER AND TABLETING EXCIPIENT

[75] Inventors: Ernest Bollin, Jr., Bear; Mark G. Fletcher, New Castle, both of Del.

[73] Assignee: E. I. Du Pont De Nemours and Company, Wilmington, Del.

[21] Appl. No.: 868,668

[22] Filed: May 30, 1986

[51] Int. Cl.⁴ ............................................. A61K 45/08
[52] U.S. Cl. .................................. 514/777; 514/960; 514/961
[58] Field of Search .................. 514/777, 960, 961

[56] References Cited

U.S. PATENT DOCUMENTS 4,206,200 6/1980 Guthohrlein et al. ................ 424/92
4,273,765 6/1981 Suhara et al. .......................... 514/54
4,457,916 7/1984 Hayashi et al. ..................... 424/101

OTHER PUBLICATIONS

Crowe et al., Science, vol. 223, 701–703 (1984).
Technology News, Apr. 18, 1986.

Primary Examiner—Shep K. Rose

[57] ABSTRACT

An improved method for preparing tablets useful in diagnostic applications, utilizing trehalose as an excipient and stabilizer, is provided.

1 Claim, No Drawings

TREHALOSE AS STABILIZER AND TABLETING EXCIPIENT

TECHNICAL FIELD

This invention relates to methods for producing stabilized tablets for diagnostic applications using trehalose as a stabilizer and excipient.

BACKGROUND ART

For convenient and efficient testing of clinical samples of biological fluids, small precise quantities of stable diagnostic reagents are needed. These reagents must be efficiently and economically prepared in large quantities without sacrificing precise delivery of the reagents. Further, the reagents should be delivered to the user in a stabilized form so as to prevent wastage of expensive reagents. The form in which the reagents are provided must allow simple rapid testing without the intervention of highly skilled technicians. One form which can meet these needs is a tablet containing all of the reagents necessary to conduct a given diagnostic assay.

A tablet of this type needs to be stable, easily prepared in a highly reproducible manner, and to dissolve rapidly upon mixing with an appropriate sample. Many difficulties have been recognized in preparing tablets containing diagnostic reagents. There must be good tablet-to-table reproducibility which, in turn, means that the dry powder blend from which the tablets are made must be highly homogeneous, the reagents must withstand the conditions used to prepare the powder blend and then the tablets, and the resulting tablet must be easily dissolved in aqueous solutions.

Preferred tablets for use in diagnostic applications are very small, preferably less than 50 mg and more preferably less than 10 mg. The need for such small tablets compounds the normally difficult problems of producing tablets useful as carriers of diagnostic reagents. The problem of inhomogeneity of the dry powder blends used to form the tablets is particularly severe since even minor inhomogeneities have a large adverse effect on the tablet-to-tablet reproducibility. This is so because of the relatively small number of dry powder particles needed to form each tablet. In order to obtain the necessary homogeneity, techniques such as certain spray freeze processes, are required (see, for example, U.S. Pat. No. 3,932,943, issued Jan. 20, 1976, and U.S. Pat. No. 3,721,725, issued Mar. 20, 1973 both to Briggs et al.).

The proportion of active reagents in a tablet formulation is often substantially smaller than that of the inert materials required to form a compact tablet of reasonable size. Further, the pure active reagents may not possess the attributes needed to insure proper formation of compressed tablets. Tablet ingredients, in general, must have some of the following attributes: flowability, lubricity, antiadherence, bulking and compactability. Certain nonactive materials can be added to a tablet formulation to contribute one or more of these attributes; these are called excipients. Any excipient used in a given application must not interfere with the desired action of the active reagents either physically or chemically. A wide variety of excipients are known and the selection of an appropriate excipient for a given application is a combination of known chemical relationships and trial-and-error experimentation.

Tablets prepared as carriers of diagnostic reagents must meet several additional criteria unique in compressed tablets. High levels of tablet-to-tablet reproducibility are required to assure accurate results. Frequently, the tablets are used to form aqueous solutions of reagents that react with components of biological fluids to form a colored product or other optically detectable signal. This requires that the excipient chosen be completely water soluble so as to avoid insoluble particles which might block the optical light thereby generating false results. Partial insolubility might also cause problems if not all the active reagents are released into the solution thereby creating tablet-to-tablet inconsistencies. Rapid dissolution is also a frequent requirement so that the desired chemical reaction can take place within a given time period. Thus, the production of a small reagent tablets requires: the ability to produce a uniform, stable, dry reagent powder, and the ability to produce a firm, precise, rapidly and easily dissolved tablet from the reagent powder.

An additional consideration in the selection of a tablet excipient is the need for it to be compatible with the process selected for preparing the dry powder blend to be tableted. The so-called S-1 spray freezing process described by Briggs et al., see above, requires that the spray solution have a relatively high percent solids content, 25-40%, in order to produce a powder of sufficient bulk density to allow for proper tableting. The preferred excipient disclosed by Briggs et al. is mannitol. Mannitol, however, can only achieve the required percent solids content when the solution is warmed to about 30° C. This elevated temperature is frequently detrimental to the active reagents, thus limiting the applicability of this technique.

Another requirement for using the S-1 technique is that the frozen droplets formed must be able to be lyophilized without melt back or formation of syrups or amorphous masses. Mannitol is preferred in this respect relative to other saccharides, such as sucrose, which while highly soluble are very difficult to lyophilize successfully.

Thus, there is a need for an improved excipient for use in preparation of a dry powder blend by the S-1 spray-freeze process which can be used to form tablets containing diagnostic reagents. This excipient should have the following properties: high solubility in aqueous solutions at or below room temperature; ability to lyophilize the resulting frozen mass without formation of syrups or amorphous masses; rapid redissolution upon addition of water or aqueous biological fluids; and the ability to enhance the stability of the active reagents to be delivered by the tablets.

In addition to active ingredients and excipients, other ingredients such as stabilizers may also be added to a tablet formulation. Stabilizers may perform two types of functions. They may permit lyophilization of certain ingredients which would not ordinarily survive lyophilization and/or they may extend the storage stability of the tablet prepared. Some stabilizers can perform only one of these functions, while others perform both. By storage stability is meant the time period after the tablet has been made during which the tablet performs acceptably. It is expected that essentially all tablets will eventually show degradation of one or more of the active ingredients, thereby limiting the storage stability.

It is known that proteins can be stabilized by lyophilization (Kozlov et al., GB 2,049,700B, issued Dec. 31, 1980). It is also known that certain poly-hydroxy compounds, including saccharides are useful in stabilizing asparaginase during lyophilization [Hellman et al., Biochem. Biophys. Acta, Volume 749, 133-142 (1983)]. Lee et al. [J. Biol. Chem., Volume 256(14). 7193-7201 (1981)] also reported that sucrose is useful in stabilizing chymotrypsin, chymotrypsinogen and ribonuclease during lyophilization. These procedures are limited in that bulk lyophilizates are not generally suitable for use in small tablets due to inhomogeneities in the dried powders.

There is a report that trehalose (α-D-glucopyranosyl-α-D-glucopyranoside) is effective in stabilizing lipid membrane structures upon lyophilization [e.g., Crowe et al., Science, Volume 223, 704-703 (1984)]. It has also been reported that trehalose is effective in stabilizing Tumor Necrosis Factor (Hayashi et al., U.S. Pat. No. 4,457,916, issued July 3, 1984) and menningococcal polysaccharides (Guthohrlein et al., U.S. Pat. No. 4,206,200 issued June 3, 1980) during lyophilization. These uses of trehalose as a stabilizer, while allowing lyophilization, did not lead to tabletable powders due to the use of bulk lyophilization techniques.

Diagnostic reagents have been stabilized in the past by lyophilization under certain conditions [Rush et al., U.S. Pat. No. 3,819,488, issued June 25, 1974] but, as before, the use of bulk lyophilization limits the usefulness of these methods because the resulting powders do not afford homogeneous tablets.

DISCLOSURE OF THE INVENTION

In the method of tableting powders for diagnostic applications, wherein the powders are the product of an S-1 process, the improvement comprises the use of trehalose as tableting excipient and stabilizer.

The S-1 process is a process for obtaining frozen droplets by spraying an aqueous solution of ingredients useful in diagnostic applications onto the surface of a moving bath of boiling perfluorocarbon liquid, followed by lyophilization of the droplets to afford dried powders suitable for tableting.

DESCRIPTION OF THE INVENTION

Surprisingly, the use of trehalose as an excipient and stabilizer in the S-1 spray freezing process fulfills all of the requirements for an improved excipient useful in producing tablets containing diagnostic reagents having good storage stability. Through the use of trehalose small, less than 10 mg, tablets useful in a wide variety of diagnostic assays have been prepared. These tablets are precise, stable, active, non-crumbling, economically feasible, conveniently dispensed, and easily and quickly dissolved. Trehalose also makes possible the facile formulation of larger reagent tablets where not all of the above criteria are critical.

The S-1 process for production of homogeneous dry powders is described by Briggs et al., U.S. Pat. No. 3,932,943, issued Jan. 20, 1976, and U.S. Pat. No. 3,721,725, issued Mar. 20, 1973, incorporated herein by reference. As described therein, an excipient to be used in this process must be highly soluble so as to achieve high solids content, generally 25-40%, so that the resulting dry powder will have a high enough bulk density to be easily processed into tablets. The excipient must also be compatible with the reagent to be included in the tablet. The preferred excipient described by Briggs et al. is mannitol. The usefulness of mannitol is limited by its limited solubility at room temperature. It is normally necessary to heat the mannitol containing solutions to about 30° C. to achieve the necessary solids content. The solution to this problem might be simple if it were simply a matter of selecting a more soluble excipient. This is not the case, however, since the excipient must also have good lyophilization properties in addition to being compatible with the reagents. Surprisingly, it has been found that trehalose and trehalose alone among sugars has all the necessary properties, being soluble up to 50% at room temperature, lyophilizing without melt back or formation of syrups or amorphous masses, and not only being compatible with a variety of diagnostic reagents but also enhancing the stability of these reagents. Tablets including trehalose as the primary excipient have also been shown to dissolve readily in aqueous solutions and to yield tablets which show excellent tablet-to-tablet reproducibility.

Trehalose is generally the component present in the largest quantity in the tablets of this invention. The active components generally make up a small percentage of the total weight for the blend, typically less than 10%. There is no minimum percentage of active components excepting that sufficient active components is included such that the tablet formed from the dried powder blend function in the desired diagnostic assay. The maximum allowed percentage of active components is only constrained by the need to prepare dried powder blends which can be readily pressed into tablets, which dissolve easily, deliver precise amounts of reagents and remain stable during storage. The maximum percentage will depend upon the specific components under consideration and will be readily apparent to the skilled artisan.

Other excipients, stabilizers and lubricants can be added to the dried powder blends in order to prepare tablets of this invention with specific properties. One instance in which another stabilizer might be included is when an oxidation sensitive active component, e.g., a thiol-enzyme requiring reducing agents for maximal activity, is included in the formulation. Other excipients and lubricants can be included to obtain dried powder blends with preferred physical, handling or tabletting characteristics. These other excipients, stabilizers and lubricants usually make up a small portion of the total weight of the blend, generally less than 25%. Larger percentages may be preferred in some instances.

The dried powder blends generally contain the following solid ingredients: active ingredients—less than about 10%, polyethylene glycol such as Carbowax 6000—approximately 7%, and trehalose—comprising the remaining solid portion. As discussed above, other formulations containing larger amounts of active ingredients or other excipients are possible, but not preferred.

The dried powder blends useful in preparing the tablets of this invention are made according to the following general procedure, variations and adjustments within the scope of this invention will be readily recognized by the skilled artisan. An aqueous solution of these components is prepared with a total solids content of about 30-35% (w/v) at ambient temperature, generally 18°-20° C. Lower temperatures, 10°-18° C., may be preferred when the active components are sensitive to heat. Still lower temperatures, 4°-10° C. are still more preferred in this respect. These sub-ambient temperatures can be accomplished by using ice/water baths or refrigerated water baths. Higher temperatures, while not preferred, can be employed if one of the active components is not easily soluble at ambient, or lower, temperatures. This contrasts with the use of mannitol as the excipient where higher temperatures, generally about 30° C., are required due to its poorer solubility when compared to trehalose. If an active ingredient of the formulation requires elevated temperatures to achieve solubility at the level required, the temperature can sometimes be lowered after its dissolution but before adding the remaining ingredients. Such a procedure may be preferred in some applications.

Following preparation of the aqueous solution of the ingredients, a dried powder blend is prepared utilizing the S-1 spray-freeze technology of Briggs et al. The dried powder can be screened through a 30-mesh screen using an oscillating granulator, although this is not required, and tabletted using any appropriate tablet press. The choice of an appropriate tablet press is generally dependent more upon the quantity and size of the tablets desired than the method used to produce the dried powder blend from which the tablets are made.

A representative formulation for a single tablet Blood Urea Nitrogen (BUN) diagnostic assay is as follows:

| COMPONENT | % COMPOSITION (W/W) |
| --- | --- |
| $KH_2PO_4$ | 7.40 |
| alpha-ketoglutarate | 0.56 |
| Triton X-100 (a surfactant) | 1.57 |
| Adenosine di-phosphate | 0.30 |
| NADH | 0.16 |
| Urease enzyme powder | 0.06 |
| GLDH enzyme powder | 0.09 |
| Ethylenediaminotetraacetic acid | 0.61 |
| Carbowax 6000 | 7.60 |
| Trehalose | 81.85 |

Small, approximately 7 mg, tablets were made from dried powder blends of this composition. These tablets were then used to determine the level of BUN in a sample by measuring the decreasing concentration of NADH. Other formulations have also been developed which allowed production of tablets useful in assays for glucose, cholesterol, triglycerides, alanine-aspartateaminotransferase, calcium, glutamate-oxalateaminotransferase, creatinine, total bilirubin and uric acid and requiring only a single tablet per assay. Tablets of this invention can be useful for assaying a wide variety of other substances such as therapeutic drugs, hormones, enzymes, electrolytes, metabolites and others.

EXAMPLE

COMPARISON OF TREHALOSE WITH OTHER SUGARS IN A BUN ASSAY

A. Preparation of Dried Powder Blends

A stock solution was prepared as follows:

The following ingredients were added in succession to 300 mL deionized water at 18°-20° C.: 4.654 g Triton X-100, 22.81 g Carbowax 6000, 22.63 g potassium phosphate, and 1.866 g ethylenediaminetetraacetic acid (EDTA). Stirring was continued to achieve complete dissolution. The pH of the solution was 4.51 and was adjusted to 7.80 with 1N potassium hydroxide.

The following ingredients were then added in succession with stirring until complete dissolution: 1.654 g alpha-ketoglutarate, 0.900 g adenosine diphosphate (ADP), and 0.463 g NADH. The pH of this solution was 7.50 and was adjusted to 7.80 with 1N potassium hydroxide solution. To the resultant solution were added 0.169 g lyophilized urease enzyme powder and 0.302 g lyophilized glutamate dehydrogenase (GLDH) enzyme powder in succession with stirring, again until complete dissolution. The pH of the solution was 7.82. The total volume of the solution was then made up to 500 mL by the addition of deionized water.

To 50.0 mL of the stock solution prepared above was added 27.04 g of trehalose dihydrate (equivalent to 24.47 g of anhydrous trehalose) and stirred until dissolved. The total volume of the solution was then made up to 100.0 mL by the addition of deionized water. This solution was then processed by the S-1 procedure.

Lyophilization of frozen droplets was carried out on a conservative schedule to allow preparation of tablets with various other sugar excipients (except sorbitol, see below) for complete comparison with the trehalose excipient of this invention. This conservative lyophilization schedule was 120 hours, starting at −30-20 C. and linearly increasing to 20° C. with time. The prolonged schedule allowed production of a sucrose blend which was not possible under practical processing parameters. When so processed, sucrose-containing blends melted back to form a syrup. The prolonged lyophilization, however, is not acceptable for routine use due to the energy inefficient and time consuming nature of the process. A practical lyophilization process normally uses an 80-hour schedule with linear temperature increase from −30° C. to 20° C. Attempts to make tablets with sorbitol as the excipient were unsuccessful even with the 120-hour schedule because of melting during lyophilization.

B. Preparation of Tablets

Tablets, approximately 7.0 mg±0.3 mg, were made from this blend on a Stokes single station tablet press Model 900 that has been modified so that the upper and lower punches twist during tablet compression. Similar tablets were prepared by substituting mannose, lactose, mannitol, glucose and sucrose for trehalose on a dry-weight basis.

C. Evaluation of Tablets

The tablets were evaluated by placing them in a clear plastic rotor having a central reservoir connected by narrow channels to cuvets to about a 2.3 cm radius. The cuvets, 35 μL in volume and cylindrical in shape with a 0.5-cm path length, contained the tablets. There were 24 such cuvets in each rotor; tablets were contained in 23 cuvets, the 24th chamber serving as a reference air blank.

A calibrator material containing a known amount of urea was prepared by adding about 18 mg/dL of urea to a bovine plasma base and then lyophilizing this mixture. This calibrator was hydrated with water to achieve a urea concentration of approximately 18 mg/dL and then used to evaluate the performance of the tablets produced containing the different excipients. This calibrator material was diluted 1:61 with water and placed in the central reservoir. The rotor was placed in a combination centrifuge/photometer and warmed to 37° C. for 2 minutes. The tablets were dissolved in the diluted calibrator by spinning the rotor at 3000 RPM, 15 spins in alternating directions. This action forced liquid into the tablet chamber/cuvet and set up a swirling motion intended to dissolve the tablets and initiate the reaction. In this case, following tablet dissolution, the kinetic measurement of BUN concentration was monitored by following the absorbance of 340 nm over the time period 30–300 seconds following tablet wetting.

A variety of indicia was examined to determine whether an excipient afforded tablets of acceptable properties.

RATE OF DISSOLUTION (Number of spins required to dissolve tablets made with different excipients)

The number of spins required to dissolve the different tablets was determined by visually examining the rotor after a given number of spins to determine when complete dissolution had taken place. It is desirable that the tablets dissolve as rapidly as possible to avoid concentration gradients resulting from incomplete dissolution which would affect the kinetics of the reaction and, consequently, the result of the assay.

| Excipient | Number of Spins to Dissolve |
| --- | --- |
| Trehalose | 6 |
| Mannose | >8 |
| Lactose | 5 |
| Mannitol | >8 |
| Glucose | >8 |
| Sucrose | 7 |

By >8 is meant that the tablet had not dissolved after 8 spins; no further spins were conducted. Glucose was not tested further.

| | Precision | | | |
| --- | --- | --- | --- | --- |
| | 15 Spins | | 8 Spins | |
| Excipient | Rate (mA/min) | CV | Rate (mA/min) | CV |
| Trehalose | 48.1 | 3.2 | 50.1 | 4.1 |
| Mannose | 42.4 | 2.1 | 48.1 | 9.5 |
| Lactose | 50.6 | 1.1 | 52.7 | 2.7 |
| Mannitol | 67.1 | 20.2 | ND | ND |
| Sucrose | 47.7 | 0.9 | 50.2 | 3.2 |

These data are mean values from eight replicate BUN determinations. All excipients tested performed acceptably with 15 spins except mannitol, which is the generally preferred excipient for use in S-1 processes. With only 8 spins, mannose also failed to perform acceptably.

| | Accelerated Stability | | | |
| --- | --- | --- | --- | --- |
| | Stored at 4° C. 15 Spins | | Stored at 25° C. 60% RH, 21 HRS 27 Spins | |
| Excipient | Rate (mA/min) | CV | Rate (mA/min) | CV |
| Trehalose | 48.1 | 3.2 | 44.5 | 9.4 |
| Mannose | 42.4 | 2.1 | 35.1 | 1 |
| Lactose | 50.6 | 1.1 | 41.8 | 13.1 |
| Mannitol | 67.1 | 20.2 | 16.7 | 4.1 |
| Sucrose | 47.7 | 0.9 | 45.4 | 1.7 |

Accelerated stability was tested by comparing tablets stored at 4° C. with those stored at 25° C., 60% relative humidity (RH) for 21 hours. These data are mean values from eight replicate BUN determinations. It was found that 15 spins was not sufficient to disssolve the tablets after exposure to this high humidity environment. It was further found that 27 spins did dissolve the tablets and this condition was used to allow assessment of stability. Those excipients where less than a 10% decrease in absorbance at 340 nm was observed were classified as being acceptable. These data indicate that only trehalose and sucrose are effective in stabilizing this formulation under the conditions tested.

| | Long Term Stability | | | |
| --- | --- | --- | --- | --- |
| | Stored at 4° C. | | Stored at 35° C. | |
| Excipient | Rate (mA/min) | CV | Rate (mA/min) | CV |
| Trehalose | 47.5 | 2 | 45.6 | 3.4 |
| Mannose | 42.7 | 3.2 | 26.9 | 9.8 |
| Lactose | 51 | 4.8 | 40.0 | 2.6 |
| Mannitol | 81.7 | 15.2 | 60.6 | 25.1 |
| Sucrose | 48.5 | 5.8 | 46.2 | 2.5 |

Tablets stored at 35° C. were compared to those stored at 4° C. These data are mean values from eight replicate BUN determinations. Those excipients where less than a 10% decrease in absorbance at 340 nm was observed were classified as being acceptable. Again, only trehalose and sucrose were effective at stabilizing this formulation under these conditions.

The quantitative results reported above can be converted to a qualitative scoring system to allow convenient comparison of the different excipients. The criteria for the scoring system are:

(1) Solubility:
   acceptable if soluble to greater than 40% (w/v) at 23° C.;
(2) Formulation:
   acceptable if lyophilizes predictably to give a free flowing dried powder blend using practical lyophilization cycles;
(3) Rate of Dissolution:
   dissolves in less than 7 spin cycles;
(4) Precision, Short Cycle (8 spins):
   Coefficient of variation less than 5%;
(5) Precision, Long Cycle (15 spins):
   Coefficient of variation less than 5%;
(6) Accelerated Stability at 25° C., 60% RH, 21 HRS:
   Less than 10% change in response; and
(7) Long Term Stability at 35° C. for 18 Days:
   Less than 10% change in response.

| SUGARS USED AS STABILIZERS/EXCIPIENTS | | | | | | |
| --- | --- | --- | --- | --- | --- | --- |
| Criteria | Trehalose | Mannose | Lactose | Mannitol | Sorbitol | Sucrose |
| (1) | + | + | − | − | + | + |
| (2) | + | + | + | + | − | − |
| (3) | + | − | + | − | − | + |
| (4) | + | − | + | − | − | + |
| (5) | + | + | + | − | − | + |
| (6) | + | − | − | − | − | + |
| (7) | + | − | − | − | − | + |

Only trehalose meets all of the requirements for a stabilizer and excipient in the production of tablets for diagnostic applications using the S-1 technology and only trehalose allows production of small tablets useful for conducting diagnostic assays with high precision, long shelf life and convenient manufacture.

We claim:

1. In the method of tabletting powders for diagnostic applications, wherein the powders are the product of an S-1 spray freezing process for obtaining frozen diagnostic droplets by spraying an aqueous solution of ingredients useful in diagnostic applications onto the surface of a moving bath of boiling perfluorocarbon liquid, followed by lypohilization of the droplets to dried powders suitable for tabletting, the improvement comprising tabletting the dried powders with the use of trehalose as tabletting excipient and stabilizer.

* * * * *